(12) United States Patent
McClellan

(10) Patent No.: US 7,722,550 B2
(45) Date of Patent: May 25, 2010

(54) BIOPSY NEEDLE WITH DIFFERENT CROSS-SECTIONAL SHAPES AND ASSOCIATED TRAP DOORS

(76) Inventor: W. Thomas McClellan, 2680 Arbor Dr., Fort Lauderdale, FL (US) 33312

( * ) Notice: Subject to any disclaimer, the term of this patent is extended or adjusted under 35 U.S.C. 154(b) by 0 days.

(21) Appl. No.: 12/180,946

(22) Filed: Jul. 28, 2008

(65) Prior Publication Data
US 2009/0030340 A1 Jan. 29, 2009

Related U.S. Application Data

(60) Provisional application No. 60/952,127, filed on Jul. 26, 2007.

(51) Int. Cl.
*A61B 10/00* (2006.01)
(52) U.S. Cl. .................. 600/567; 600/564
(58) Field of Classification Search .......... 600/564, 600/567
See application file for complete search history.

(56) References Cited

U.S. PATENT DOCUMENTS

| 3,173,414 | A | * | 3/1965 | Guillant | 600/565 |
|---|---|---|---|---|---|
| 4,282,884 | A | * | 8/1981 | Boebel | 600/564 |
| 4,651,751 | A | | 3/1987 | Swendson et al. | |
| 4,651,752 | A | * | 3/1987 | Fuerst | 600/567 |
| 4,781,202 | A | * | 11/1988 | Janese | 600/567 |
| 5,462,062 | A | * | 10/1995 | Rubinstein et al. | 600/567 |
| 5,827,305 | A | * | 10/1998 | Gordon | 606/159 |
| 5,885,226 | A | | 3/1999 | Rubinstein et al. | |
| 6,110,128 | A | | 8/2000 | Andelin et al. | |
| 6,827,692 | B2 | * | 12/2004 | Castellacci | 600/567 |
| 2002/0151821 | A1 | | 10/2002 | Castellacci | |
| 2005/0222520 | A1 | | 10/2005 | Faciszewski | |

OTHER PUBLICATIONS

International Search Report and Written Opinion dated Nov. 3, 2008.

* cited by examiner

*Primary Examiner*—Max Hindenburg
*Assistant Examiner*—Sean P Dougherty
(74) *Attorney, Agent, or Firm*—Laurence A. Greenberg; Werner H. Stemer; Ralph E. Locher

(57) ABSTRACT

A biopsy needle has a forward needle opening that can be closed off with a trap door. The trap door is pivotally mounted to a flat top surface inside the needle opening. As the needle is extracted, a forward blade of the trap door cuts into the biopsy tissue and the trap door pivots about a pivot axis extending transversely to a longitudinal direction of the needle. The trap door is configured to match a contour of the top surface and an adjacent curve of the needle opening to maintain the needle substantially open when the trap door is in the open position and to close the forward needle opening when the trap door is in the closed position and the biopsy tissue specimen is entrapped inside the needle.

12 Claims, 16 Drawing Sheets

BIOPSY NEEDLE WITH DIFFERENT CROSS-SECTIONAL SHAPES AND ASSOCIATED TRAP DOORS

CROSS-REFERENCE TO RELATED APPLICATION

This application claims the priority under 35 U.S.C. §119 (e) of my copending provisional patent application No. 60/952,127, filed Jul. 26, 2007.

BACKGROUND OF THE INVENTION

Field of the Invention

The invention relates to biopsy needles for obtaining a tissue biopsy specimen. More specifically, to invention pertains to improved doors for such needles.

The present description pertains to a further improvement in my biopsy needle invention described in my copending patent application Ser. No. 11/361,422, filed Feb. 24, 2006. The former application is herewith incorporated by reference in its entirety. There, there is described a biopsy needle system with a carrier, a trocar to be inserted into the carrier for percutaneous insertion to a biopsy site, and a biopsy needle to be inserted into the carrier. The biopsy needle enters the biopsy site and, upon being pulled back, cuts a biopsy specimen from the side.

The forward end of the needle, i.e., the insertion and specimen collection end, is provided with a type of one-way trap door. During the insertion into the tissue, the door should merge into the side wall of the needle opening and thus provide as much opening cross-section as possible. During the extraction, the door should close the needle opening to a large extent and also provide for a stiff wall.

The previous door designs of this application utilize live hinge technologies developed by the unique laser cutting technique of overlapping patterns or column formations in the door material which by their direction and configuration converted these formed columns of material, from a destructive "flexing or bending" action into columns of a more tolerated "torsion twisting". This created a much improved function or true live hinge out of non-pliant material and markedly reduced flexing resistance and increased cycle life.

The singular disadvantage of this design is the increased production costs of the macroscopic laser formation or cutting of the required column forming patterns.

BRIEF SUMMARY OF THE INVENTION

It is accordingly an object of the invention to provide a door for a biopsy needle which overcomes the above-mentioned disadvantages of the heretofore-known devices and methods of this general type and which provides for further variations and improvements of the door design and forming technique.

With the foregoing and other objects in view there is provided, in accordance with the invention, a biopsy needle assembly, comprising:

a needle having a forward needle opening with a substantially flat top surface and a given cross-sectional shape;

a trap door pivotally mounted to the substantially flat top surface inside the needle opening, for pivoting about a pivot axis extending transversely to a longitudinal direction of the needle between an open position and a closed position;

the trap door being configured to match a contour of the top surface and an adjacent curve of the needle opening to maintain the needle substantially open when the trap door is in the open position, and to substantially close the forward needle opening when the trap door is in the closed position.

The needle cross-section may be circular, oval, or polygonal, apart from the top surface.

In accordance with another feature of the invention, the trap door is formed of a sheet metal material having a thickness in the range from 0.001 to 0.01 inches, preferably from 0.001 to 0.002 inches.

In accordance with an added feature of the invention, the trap door is provided with reinforcements in a central portion thereof. Preferably, the reinforcements are ridges extending substantially in the longitudinal direction and resisting a flexion of said trap door in a transverse direction.

Preferably, the trap door is provided with reinforcements in the form of stamped or rolled elevations of rounded or V-shaped columns. That is, the central door area has I-beam type reinforcements extending in a longitudinal direction and defining a length of a portion of the trap door having a relatively high stiffness.

In accordance with an added feature of the invention, the trap door is formed with a flat end portion attached to the flat top surface and a live hinge adjacent the flat end portion, for pivoting the trap door between the closed and open positions. In a preferred embodiment, the trap door is also formed with two longitudinal live hinges enabling two lateral edges to be folded back when the trap door is in the open position.

By definition, the longitudinal live hinges are formed to define a flexing direction and a torsion direction. In the flexing direction, the structure provides relatively strong resistance to bending and in the torsion direction it provides relatively weak resistance to bending.

In accordance with an added feature of the invention, the trap door is provided with reinforcements in a central portion. The reinforcements may be ridges extending substantially in the longitudinal direction and resisting a flexion of the trap door in a transverse direction.

The door is similar in shape, size, configuration, material and function to prior designs. The primarily significant difference is in its front surface to back surface thickness and also therefore its increased innate or general flexibility. In the design described in my application Ser. No. 11/361,422, the stainless steel or other suitable material was in the general range of 0.040 to 0.060 inches thickness and the several areas requiring increased flexibility where created by the configured contours of torsion causing lasered columns while leaving the central area requiring increased stiffness unaltered or uncut.

The new door design reverses these innate properties of the parent material by decreasing the thickness of the suitable door material to the general range of 0.001 to 0.002 inches in thickness—or other suitable thicknesses—which naturally yield the required outer contours of increased flexibility without laser patterning and the central area of required increased stiffness is more simply accomplished by the formation through stamping or rolling of elevated "half round" or "v" shaped vertically oriented columns creating one or more "I beam type" vertical plane reinforcements to this central area. The purpose of this central area of relative stiffness is to confine and control the length of the required areas of flexing and thereby controlling the ultimate length, safety and closed position of the biopsy needle cut-off door.

This description shows that in the needle biopsy door portion of my copending application a new design and method for creating the doors' required differential flexibility can be accomplished. The various advantages are achieved by making the small area stiffer in a less costly process while still retaining the larger areas of suitable relative flexibility.

Other features which are considered as characteristic for the invention are set forth in the appended claims.

Although the invention is illustrated and described herein as embodied in a biopsy needle and trap door for the biopsy needle, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

DESCRIPTION OF A PREFERRED EMBODIMENT OF THE INVENTION

Figure 1A:
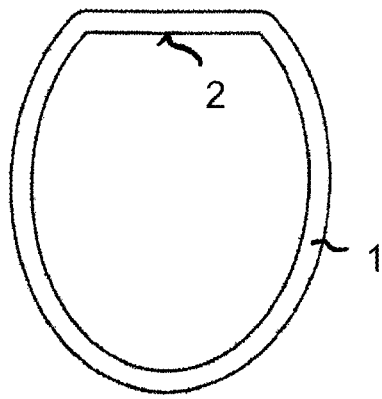
FIGS. 1A, 1B, and 1C show three variations in the cross-section of the biopsy needle tube or body.
Figure 1B:
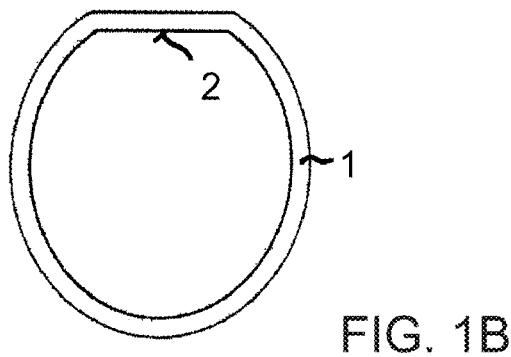
Figure 1C:
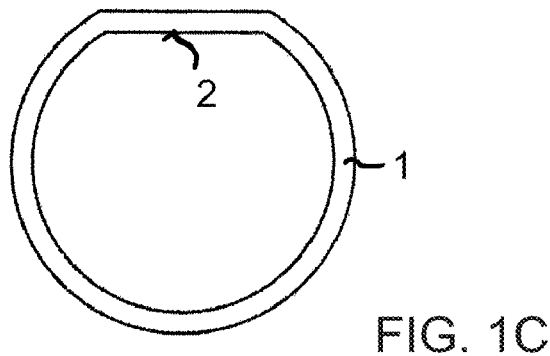

Referring now to the figures of the drawing in detail and first, particularly, to FIGS. 1A, 1B, and 1C thereof, there are seen three variations of cross-sectional shapes of a biopsy needle 1. Of the three, FIG. 1A shows the more oval shape. FIG. 1B is more rounded, and FIG. 1C is fully circular (i.e., cylindrical needle) with a flat top wall. All of the shapes share a substantially flat top wall 2 for attachment of the door hinge. The embodiment of FIG. 1B is believed to provide for the best compromise between aesthetics and science, in that the self-alignment of the door is preserved on closing. The opening is approximately 95% circular, as opposed to FIG. 1A, which is approximately 90% circular, and FIG. 1C, which is approximately 98% circular.

The description and the claims refer to relative positions and directions as "top" and "vertical" or "horizontal. It should be understood that these relative indications pertain only to the drawing views and are provided for the ease of description. The needle, of course, may be operated in any relative position and its functionality is not impaired or changed if these alignments or orientations are changed.

Figure 2:
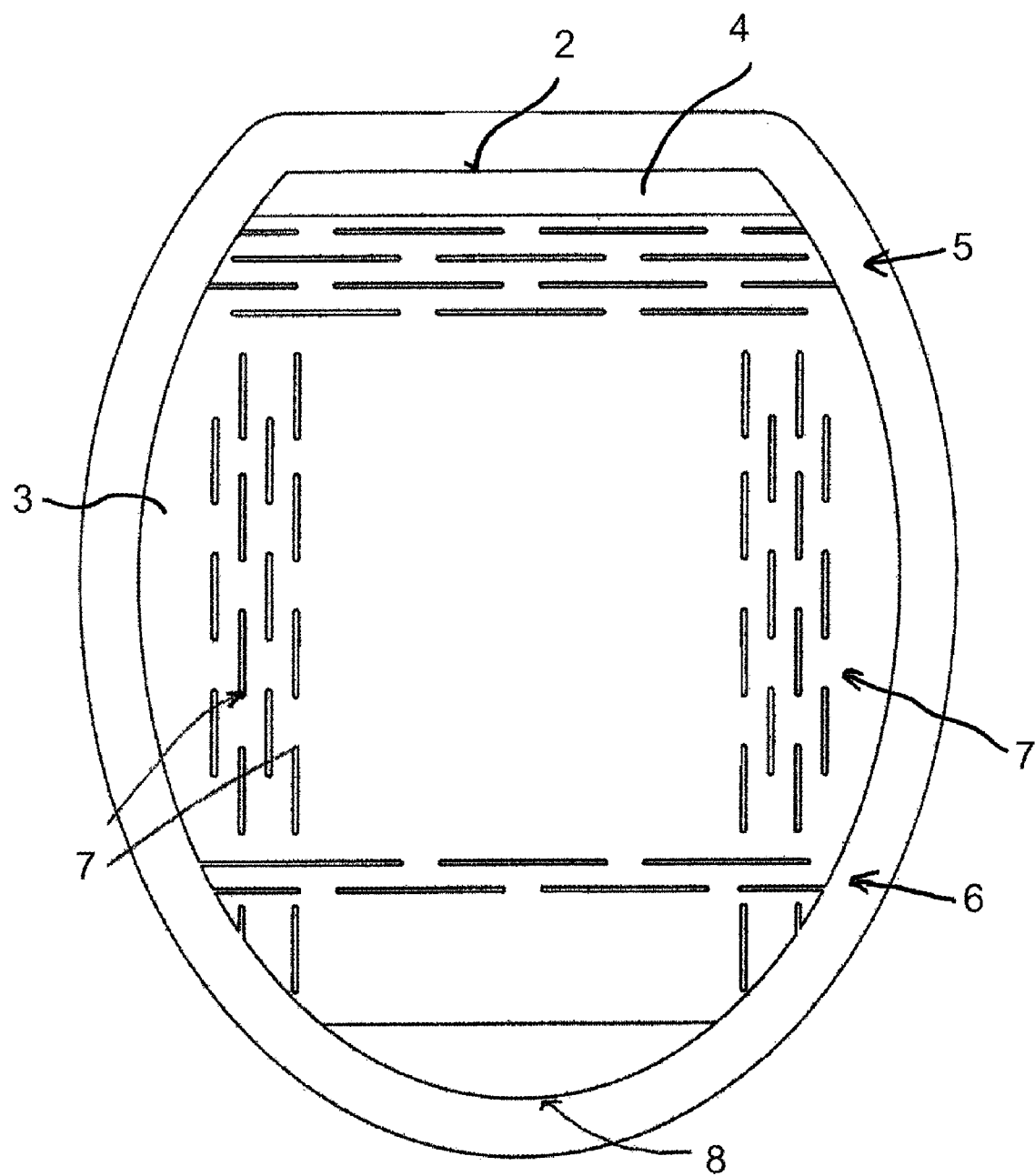
FIG. 2 is an end view of a door and the needle body.

FIG. 2 shows an end view of the biopsy needle 1 (i.e., the oval shape of FIG. 1A) with a trap door 3 in its closed position. The trap door 3 has a flat end portion 4 which is laser welded to the top wall 2 of the needle 1 along a pivot axis A. Further, the door 3 is formed with several live hinges, namely, an upper horizontal live hinge 5, a lower horizontal live hinge 6, and two vertical live hinges 7.

The upper live hinge 5 allows the door to pivot between the open position—during the insertion into the tissue—and the closed position, as illustrated. It is most important for the door 3 to be able to closely match the marginal shapes of the needle 1 in both positions. That is, the two vertical hinges 7 must be so soft as to allow the door 3 to adapt to the relatively steep curvature of the needle opening adjacent the flat top wall 2 in the open position. At the same time, the two vertical hinges 7 must allow the lateral wings of the door 3 to spread open so as to close the opening during the extraction of the tissue sample. At the same time, of course, the door must be so sturdy as to allow the tissue to be cut during extraction and to close the door to retain the tissue sample. If the door were allowed to collapse backwards, of course, the tissue would be damaged but no sample would be extracted. On the other hand, if the door did not close the biopsy needle lumen to a large extent, it could not be assured that the tissue sample did indeed remain in the needle during extraction or, in the case of very soft tissue, that enough tissue could be extracted.

Figure 3:
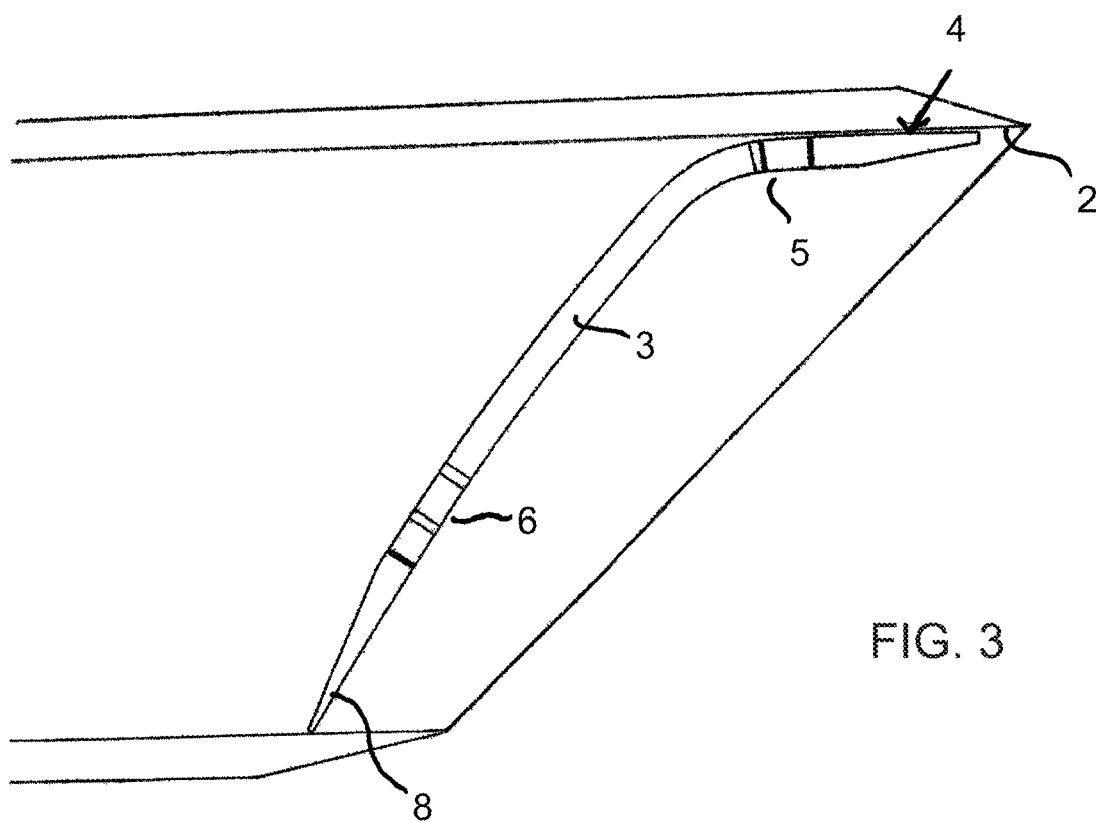
FIG. 3 is a longitudinal sectional view showing an exemplary embodiment of a door in a closed position.

The illustration of FIG. 3 again shows the door in its closed position. The upper hinged portion 4 is attached to the top wall 2 of the needle 1. The central part of the trap door is relatively stiff so that the trap door cannot collapse out of the needle lumen, towards the right in FIG. 3. The novel live hinge system proposed by the inventor allows the side wings to be locked in the extended position and the door to be flexible as thin plastic along one axis, while being strong as steel in the transverse axis. The door 3 is formed with a tip 8 which serves a dual purpose. The tip 8 is formed as a sharp cutting blade which, as the needle is extracted, initiates the closure of trap door 3 and at the same time cuts the tissue biopsy sample from the biopsy site.

Figure 4:
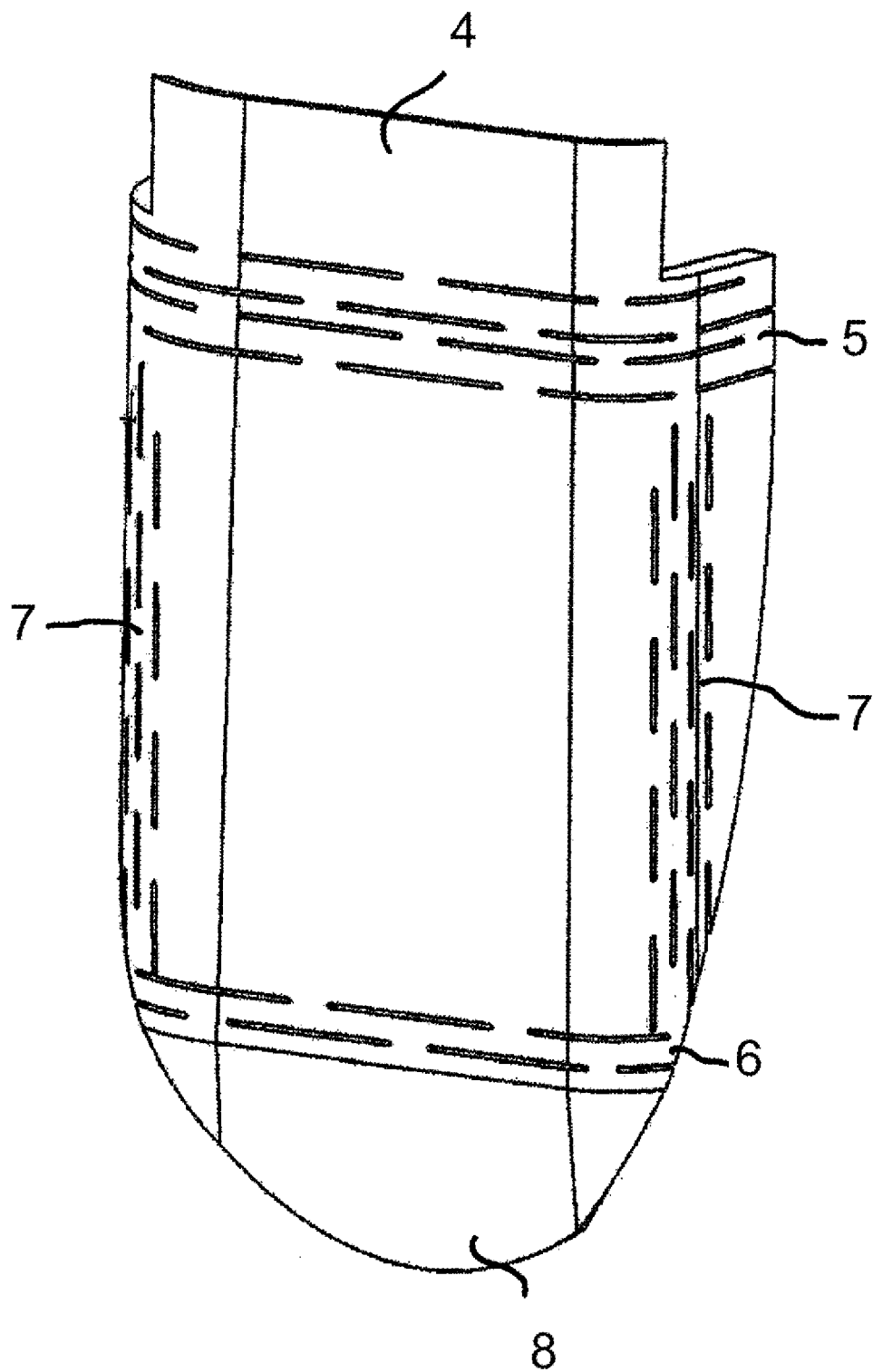
FIG. 4 is a perspective view of an exemplary door, shown with bent-over side walls that adapt to the contour of the needle body.
Figure 5:
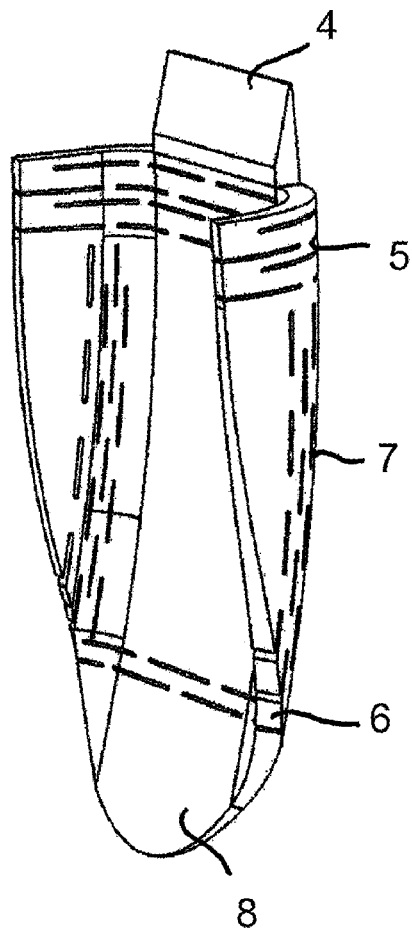
FIG. 5 is a rear perspective view of a similar door.
Figure 5A:
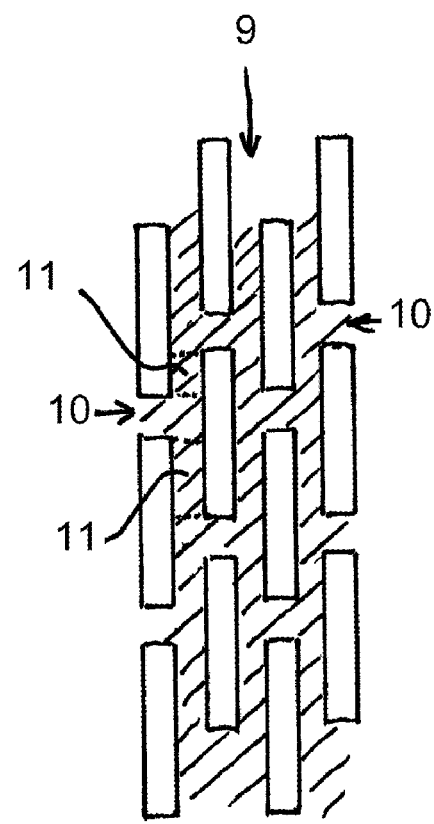

FIGS. 4 and 5 illustrate the trap door 3 in its "open" position, as it would be shaped in the oval embodiments of FIG. 1A or 1B. Here, the lateral live hinges 7 are fully bent, while the horizontal hinges 5 and 6 are fully straight. Yet more importantly, the laser-machined hinges allow virtually no flex along their longitudinal extent, while they allow ready torsion in the transverse direction. This flex-versus-torsion phenomenon is best understood when reviewing the remaining material bridges formed between the laser voids of the hinges. As shown in FIG. 5A, the longitudinal (vertical) bridges 9 are continuous along the entire hinge. That is, they are not interrupted by voids and, accordingly, they maintain a considerable amount of rigidity in that direction. The transverse (horizontal) bridges 10 are discontinuous, i.e., they are interrupted along their extent. As a result, the material may be easily bent at the voids and the metal matrix is subjected to torsion at the connecting portions 11. The connecting portions 11 are defined at the longitudinal overlap between the voids. Steel sheets with a thickness in the neighborhood of 1 to 20 mils are typically very resistant to flexing but they are less resistant to torsion. In this case, the material bridges 9 are continuous and resist against flexing, while the bridges 10, 11 are a combination of the two. The bridges 10 are subject to flexing, while the bridges 11 are subject to torsion. Accordingly, the hinge of FIG. 5A bends quite readily in the transverse direction (horizontal in FIG. 5A), while it is very resistant to bending in the longitudinal direction (vertical).

Figure 6:
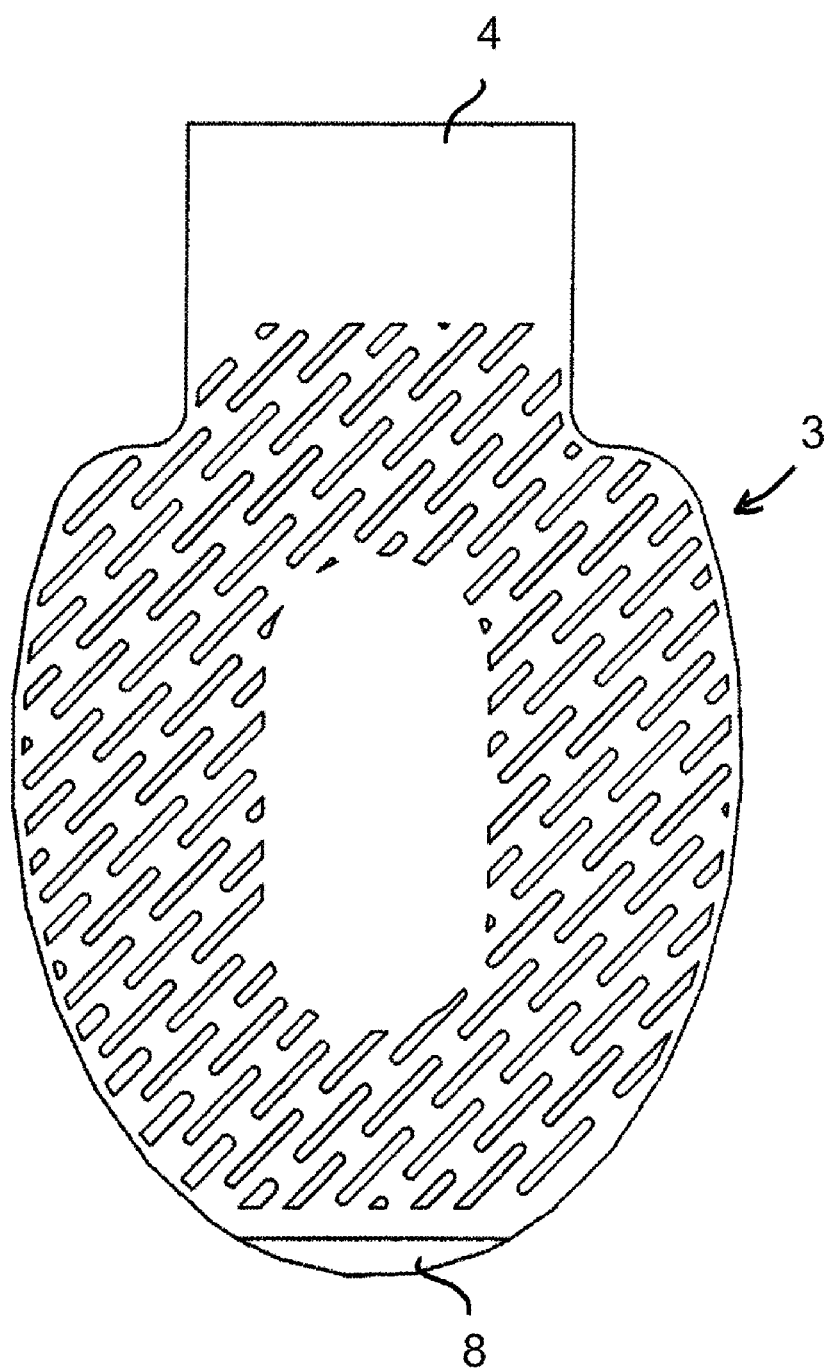
FIG. 6 is a frontal view of laser cut patterns described in copending application Ser. No. 11/361,422, forming a torsion hinge end cutting biopsy needle door.

FIG. 6 shows a laser cutting pattern for a door as it is described in my copending application Ser. No. 11/361,422. The door illustrated here is a torsion hinge end cutting biopsy needle door 3. This embodiment of the door uses slightly thicker sheet material and its torsion/flex behavior is entirely defined by its laser cut distribution. The central portion of the door 3 is not provided with any voids, so as to assure its full integrity and stability in the center, where no bending is required, or desired, in the closed position and in the open position of the door.

Figure 7:
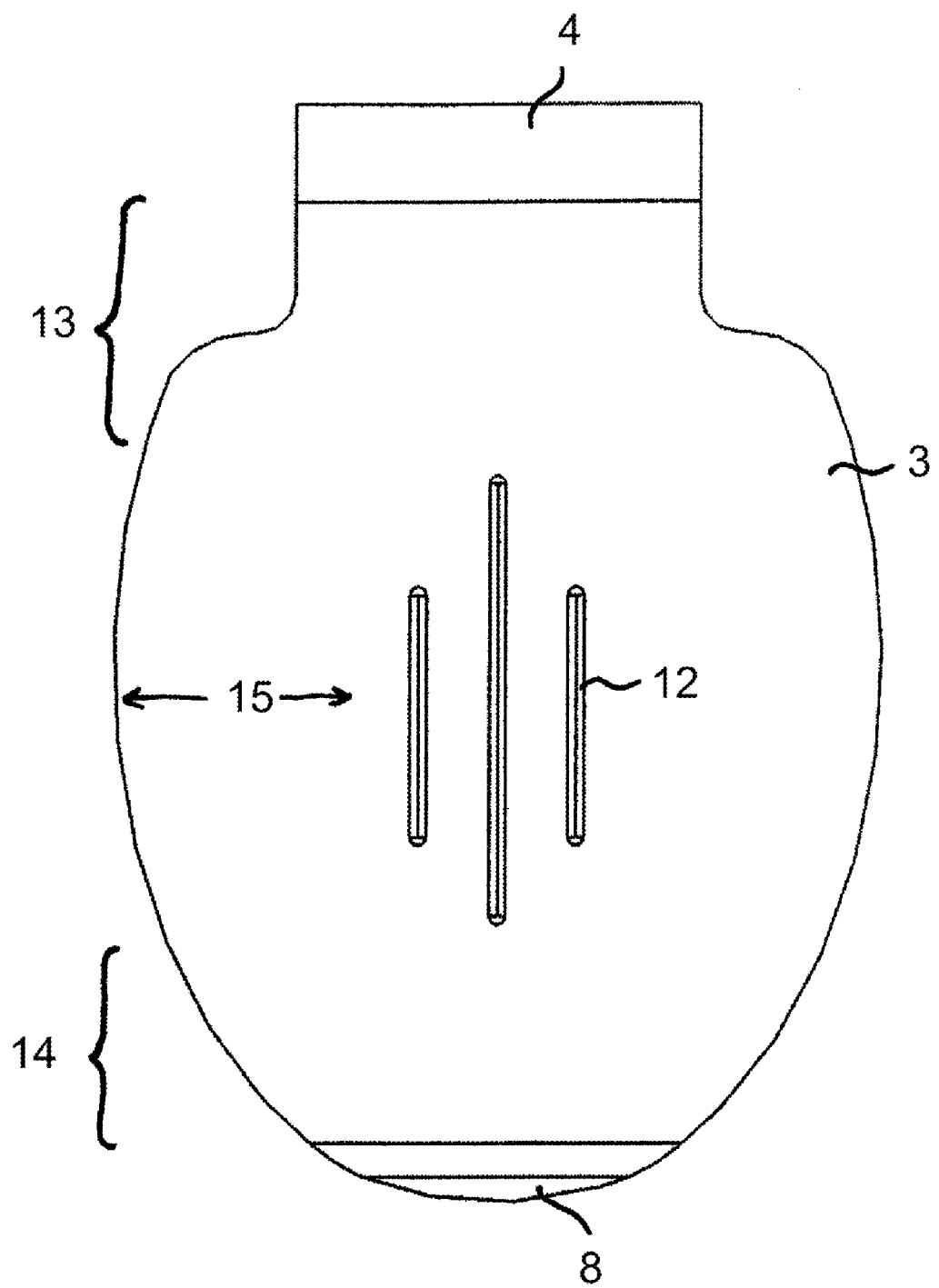
FIG. 7 is a frontal view of an exemplary embodiment of the door, indicating a method for forming the door.

FIG. 7 is a frontal view of an exemplary embodiment of a new door 3. Here, the door 3 is formed from extremely thin sheet material (e.g., 0.001 to 0.002 in steel sheet). In order to assure the central field integrity of the door, the sheet is provided with reinforcements 12. These may be embedded ridges, folds, or welded-on ridges. The top portion 4 is used to fuse or weld the trap door 3 to the top wall 2 of the biopsy needle 1. Just below the attachment portion 4, the door is provided with an area 13 of controlled flexion for closing. Similarly, the lower portion 14 just above the tip 8 forms a further area of controlled flexion for closing. The tip 8 is slightly turned down so as to assure that the tip 8 catches upon extraction and digs/cuts into the tissue specimen. The lateral wings of the trap door 3 also are defined with controlled flexion so as to assure that the door may be tightly parked within the needle. At the same time, the wings are sufficiently stiff so as to assure that the biopsy tissue specimen is safely retained in the needle upon extraction.

Figure 8:
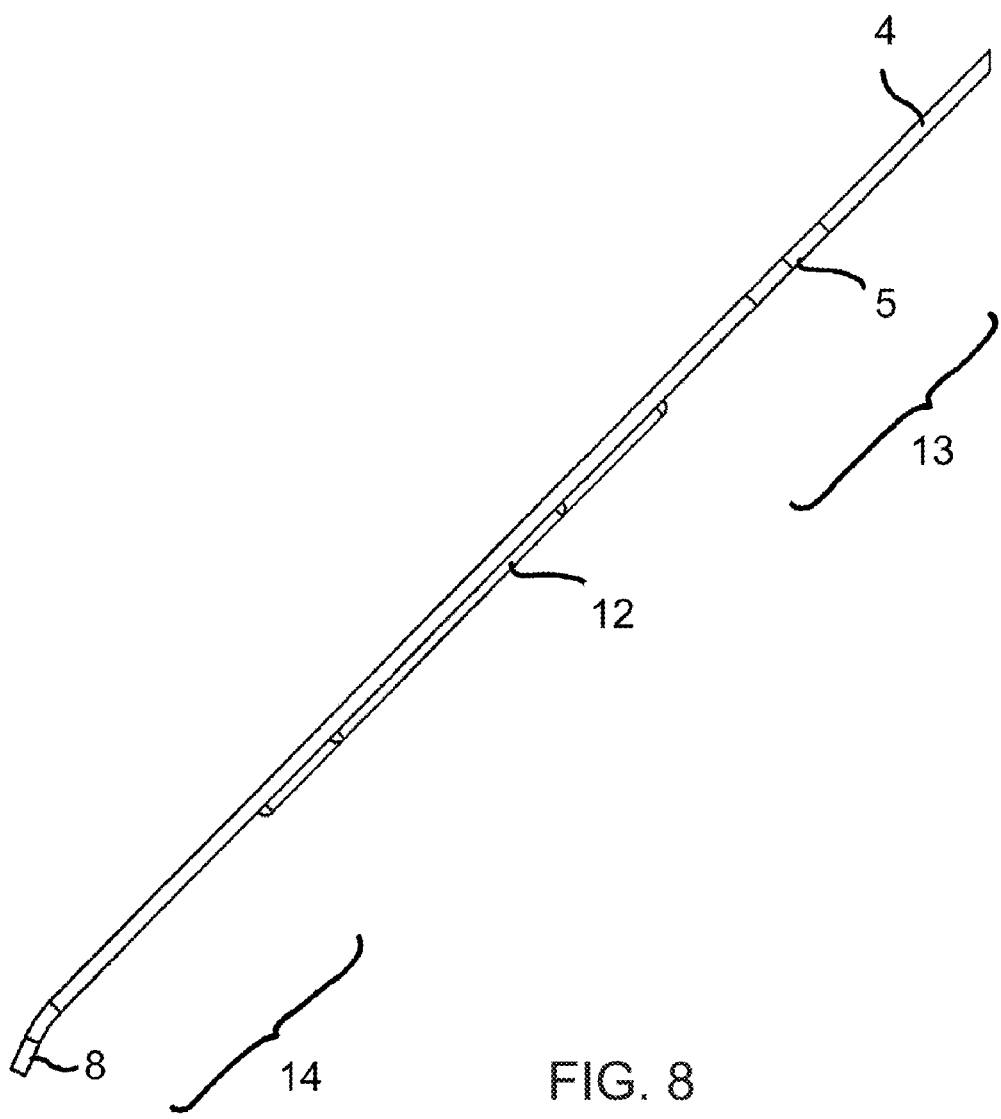
FIG. 8 is a lateral view of new door variation.

FIG. 8 is a longitudinal section through the trap door 3 of FIG. 7 in its relaxed position as it would be parked along the top wall of the needle.

Figure 9:
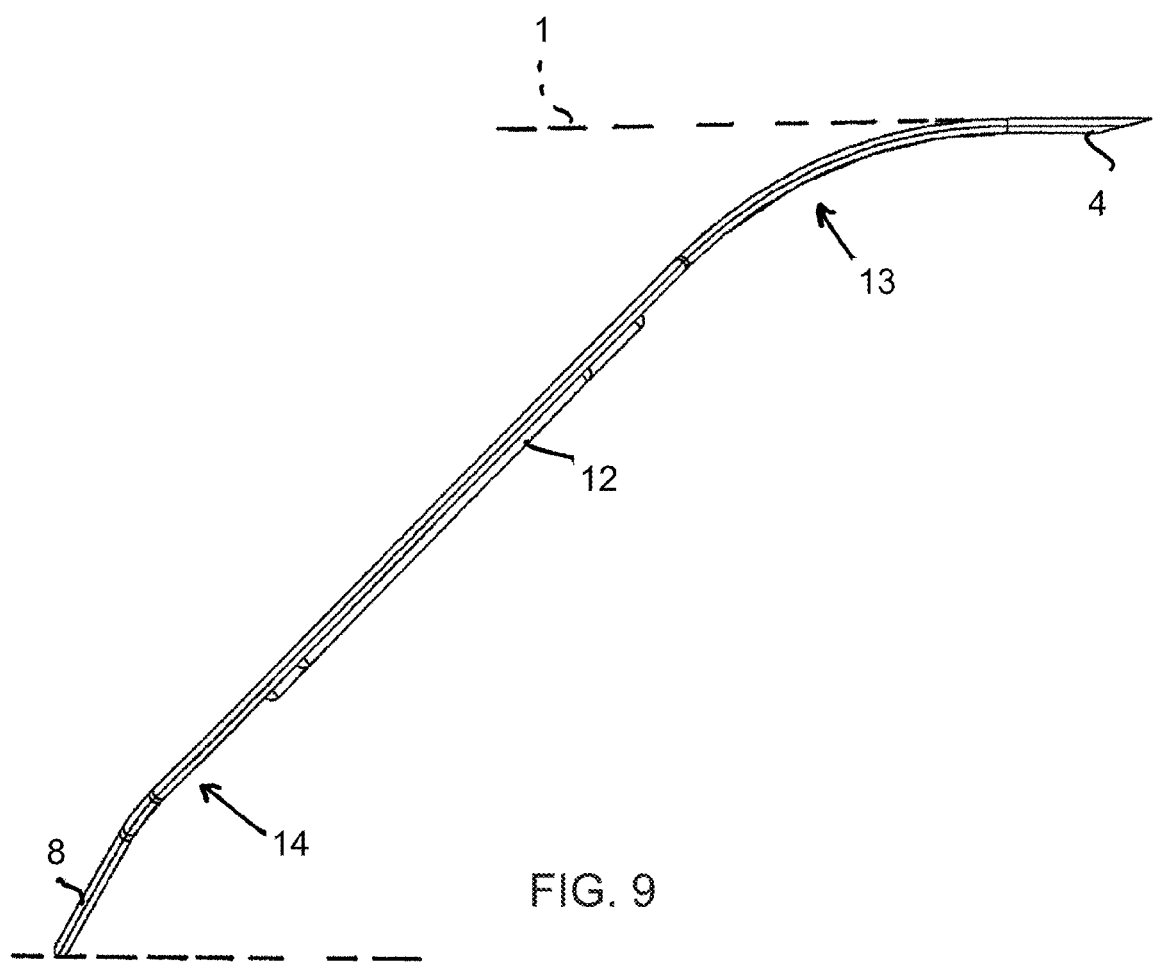
FIG. 9 is a lateral view in the closed configuration.

FIG. 9 is a similar view of the trap door 3 in its closed position. The top wall and the bottom wall of the needle 1 are indicated in dashed lines.

Figure 10:
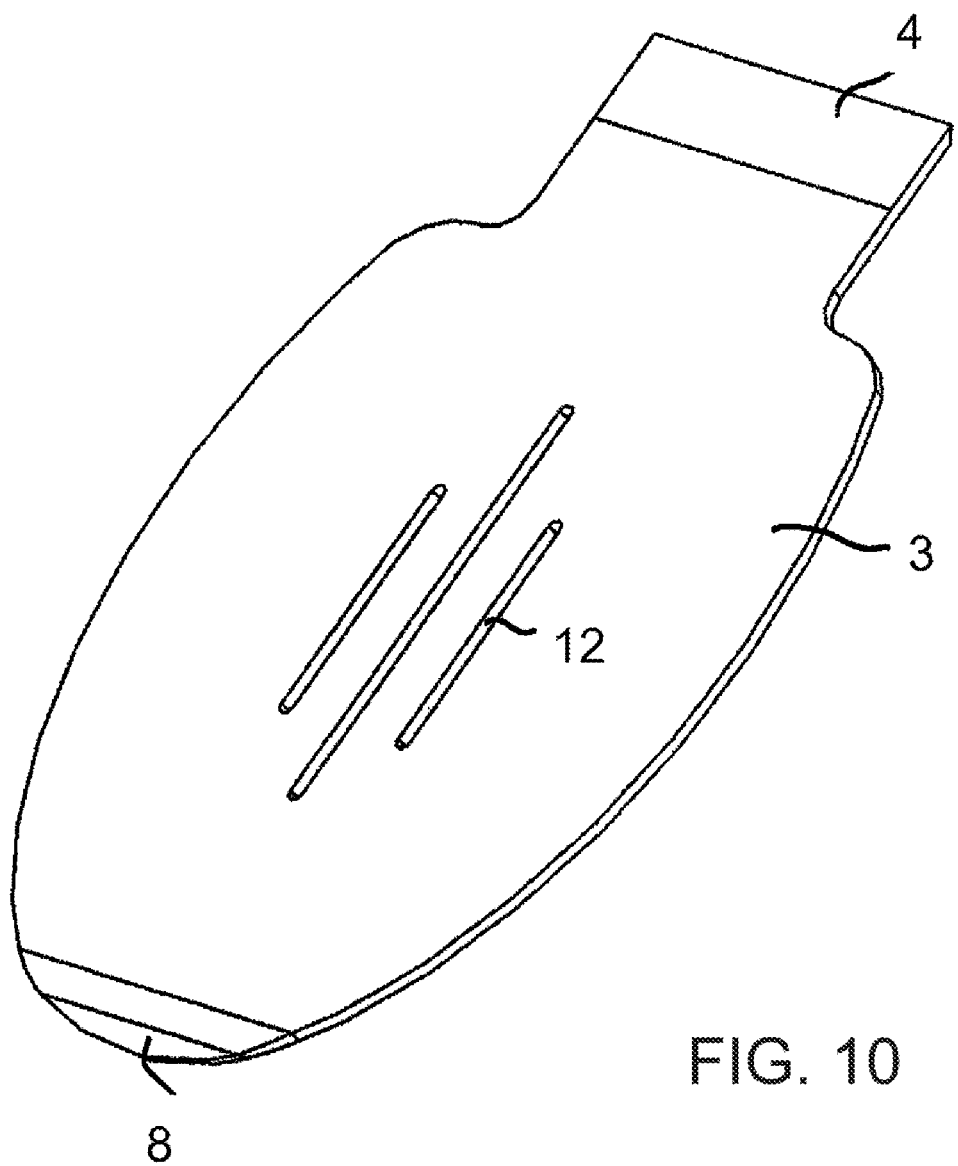
FIG. 10 is a frontal oblique view.
Figure 11:
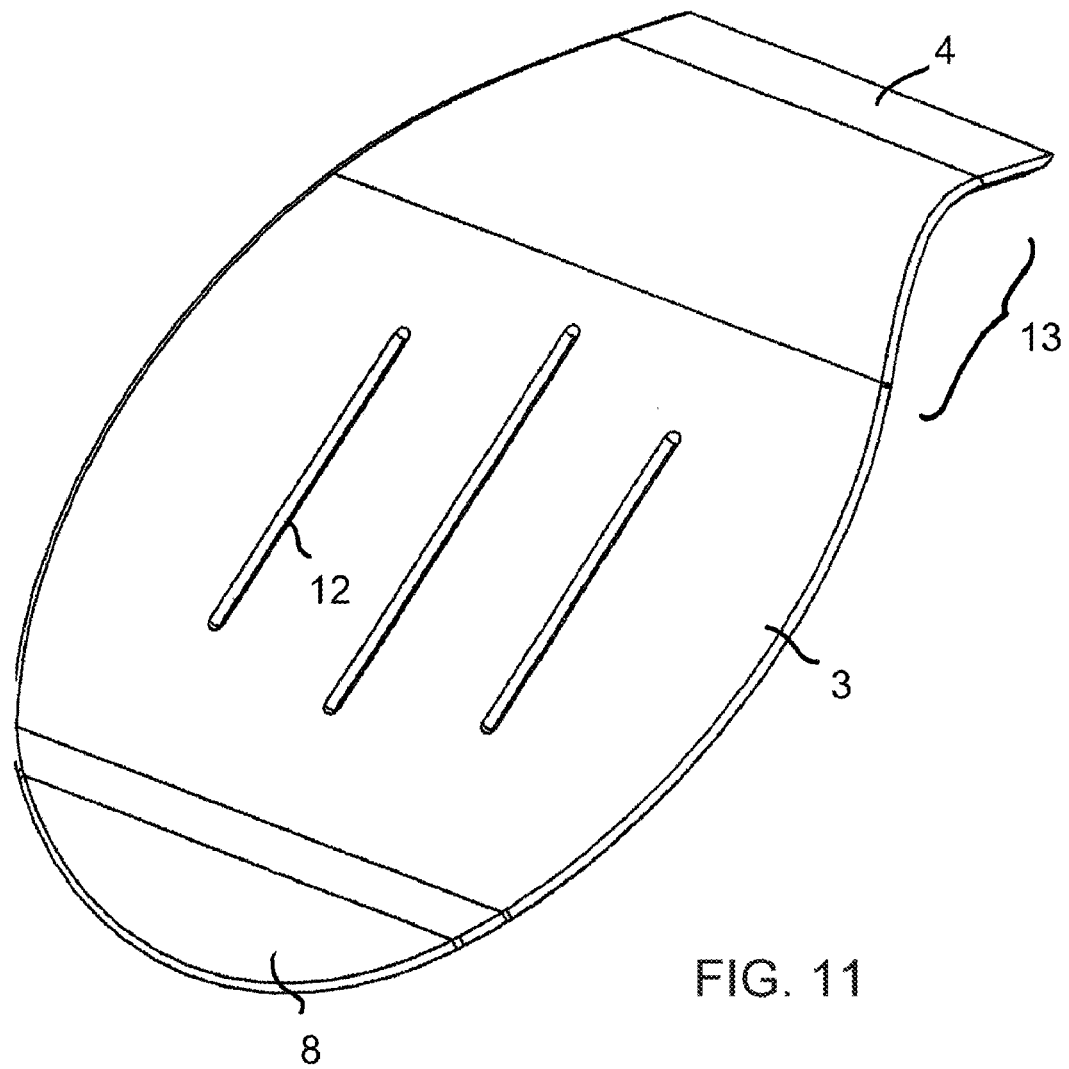
FIG. 11 is a frontal oblique view in the closed configuration.

FIGS. 10 and 11 are perspective views that correspond to FIGS. 8 and 9, respectively. FIG. 10 shows the door 3 in its relaxed position, while FIG. 11 shows the door 3 in its closed position. The area 13 is flexed downwardly, while the area 14 is straight. The latter, area 14 for controlled flexion is subject to longitudinal flexing substantially only during the extraction procedure. As the needle is extracted after having been inserted into the tissue, the turned-down tip 8 first cuts into the tissue. This holds the tip 8 back and the extraction resistance causes the trap door 3 to close. First, the area 14 is flexed downwardly, until the entire door 3 is inclined downwardly, with the area 13 flexed downwardly. As the extraction procedure is continued, the door 3 assumes its position as illustrated in FIGS. 9 and 11 (see, also, FIGS. 12, 13). Once the tissue sample is completely separated from the host tissue, there is very little further stress on the door 3 and the door 3 retains the tissue sample safely inside the needle. It is clear that the amount of closure (i.e., the accuracy of the fit between the outer edges of the door and the inside wall of the needle) required here, is driven by the type of tissue specimen to be biopsed. Generally, it may be stated that the softer the tissue, the more accurate the fit should be.

Figure 12:
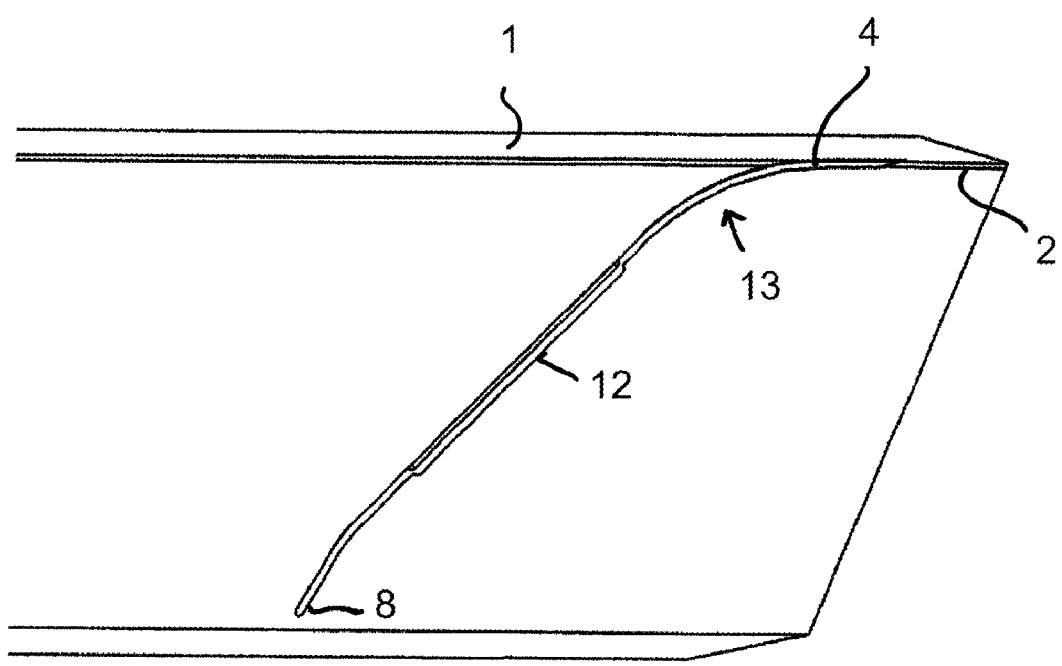
FIG. 12 is a lateral section view of the new door mounted within the needle shown in the closed position.
Figure 13:
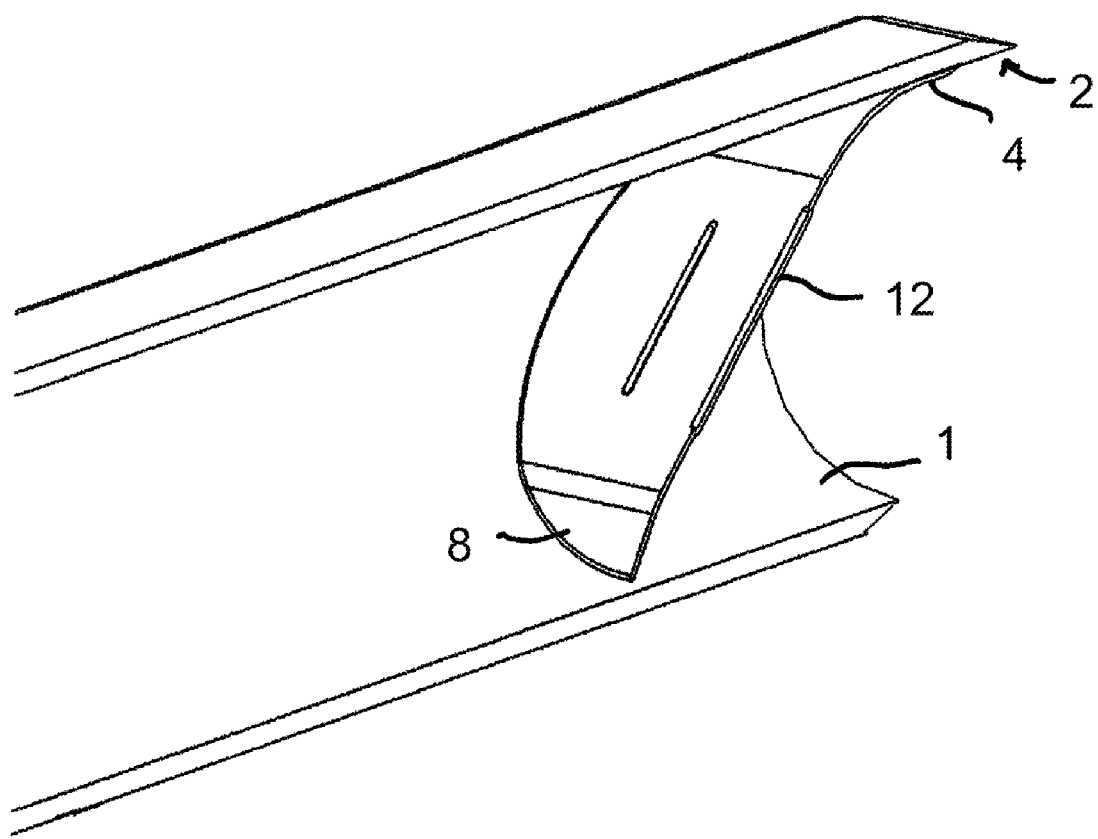
FIG. 13 is an oblique sectional view showing the door in the closed position.

The embodiment illustrated in FIG. 7—and again in FIGS. 12, 13 inside the needle body—is accurately matched to the contour of the needle 1. The closure, therefore, is nearly complete.

Figure 14:
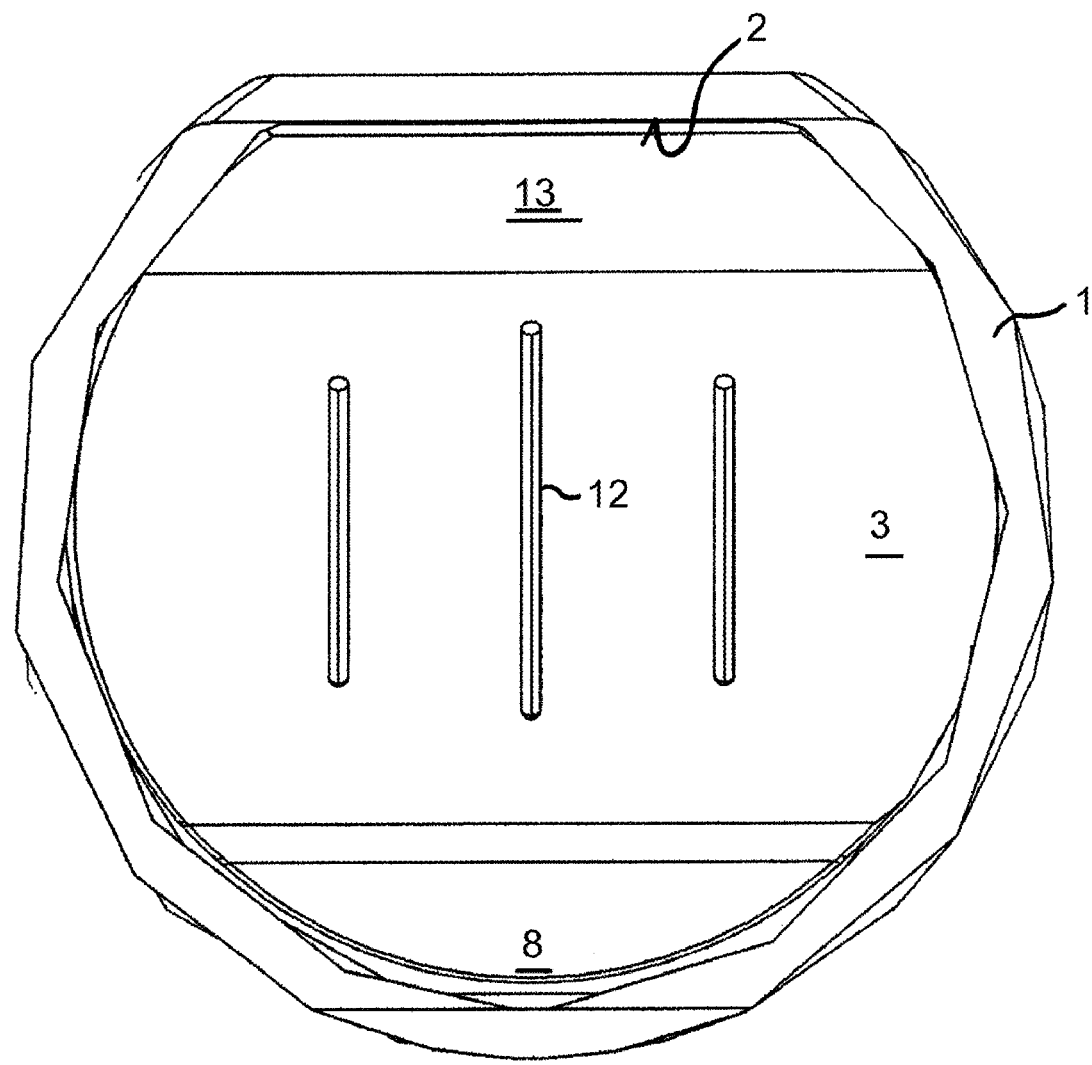
FIG. 14 is an end view of a biopsy needle with the new door in the closed position.

The embodiment illustrated in FIG. 14 pertains to a rounded trap door 3 and a polygon shaped needle. As shown, even if the two contours are not completely matched, the degree of closure is still quite high. The embodiment of FIG. 14 is satisfactory for most soft to medium soft tissue samples.

Figure 15:
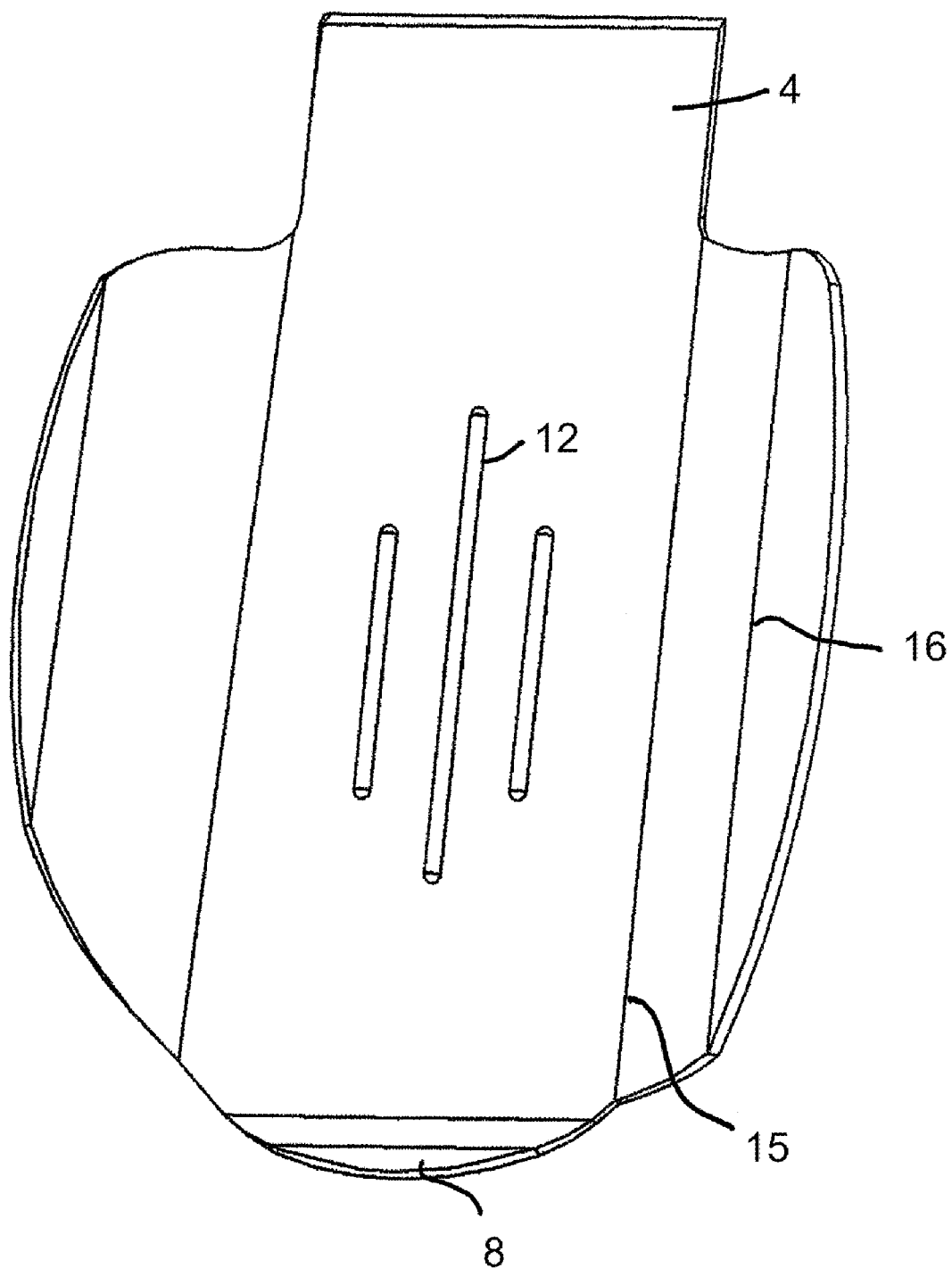
FIG. 15 is a frontal view of the new door shown in the open configuration with the lateral edges or "wing" flexed for "parking" or nesting within the internal biopsy needle contour.
Figure 16:
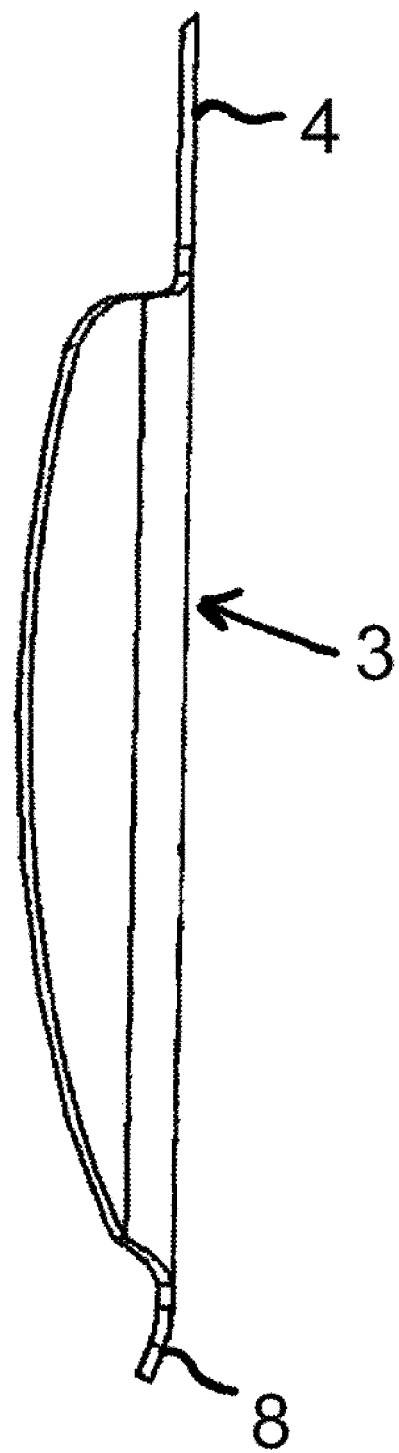
FIG. 16 is a lateral view of the new door shown in the open position with the lateral wings flexed for "parking" or nesting with in the internal needle contour.

FIG. 15 illustrates an embodiment of the door 3 that is carefully matched to a polygonal needle opening. Besides, the embodiment may also be employed in an oval or circular needle opening. The lines 15 and 16 substantially correspond to the location of an edge inside the needle, so that the door 3 folds in accordance with the polygonal shape. The lines therefore indicate that the material is weakened there (e.g., laser scoring, mechanical scoring, slight material removal, etc.) so as to define its preferred bending line and defining the lateral wings. Here, the lateral wings are folded back, indicating that the door 3 is in its open position, parked against the needle wall. FIG. 16 is a side elevation of the door in the same position. The reinforcements 12 of FIG. 15 are attached on the backside of the door 3, opposite the tissue sample. It will be understood that the reinforcement 12 may be formed on the back and/or on the front side of the door 3.

The invention claimed is:

1. A biopsy needle assembly, comprising:
    a biopsy needle having a forward needle opening, said forward needle opening having a top surface being substantially flat transversely to a longitudinal direction of said needle and said forward needle opening having a given circumscribed cross-sectional shape;
    a trap door having a flat end portion pivotally mounted, hinged and connected to said substantially flat top surface inside said forward needle opening, for pivoting about a pivot axis extending transversely to said longitudinal direction of said needle between an open position caused by insertion of said needle into tissue and a closed position caused by extraction of said needle while cutting a tissue sample;
    said trap door being configured to match a contour of said flat top surface and an adjacent curve of said needle opening to maintain the needle substantially open when said trap door is in the open position, and to substantially close the forward needle opening when said trap door is in the closed position.

2. The biopsy needle assembly according to claim 1, wherein said biopsy needle has a cross-sectional shape selected from the group consisting of circular, oval, and polygonal, apart from said flat top surface.

3. The biopsy needle assembly according to claim 1, wherein said trap door is provided with reinforcements in a central portion thereof.

4. The biopsy needle assembly according to claim 3, wherein said reinforcements are ridges extending substantially in the longitudinal direction and resisting a flexion of said trap door in a transverse direction.

5. The biopsy needle assembly according to claim 1, wherein said trap door is formed of a sheet metal material having a thickness in a range from 0.001 to 0.01 inches.

6. The biopsy needle assembly according to claim 5, wherein said trap door material has a thickness in a range from 0.001 to 0.002 inches.

7. The biopsy needle assembly according to claim 1, wherein said trap door is provided with reinforcements in a central portion thereof, said reinforcements being stamped elevations or rolled elevations of rounded or V-shaped columns.

8. The biopsy needle assembly according to claim 1, wherein said trap door is provided with I-beam reinforcements in a central portion thereof extending in a longitudinal direction and defining a length of a portion of said trap door having a relatively high stiffness compared to other portions of said trap door.

9. The biopsy needle assembly according to claim 1, wherein said trap door is formed with a flat end portion attached to said flat top surface and a live hinge adjacent said flat end portion, for pivoting said trap door between the closed and open positions.

10. The biopsy needle assembly according to claim 9, wherein said trap door is formed with two longitudinal live hinges enabling two lateral edges to be folded back when said trap door is in the open position.

11. The biopsy needle assembly according to claim 10, wherein said longitudinal live hinges are formed to define a flexing direction and a torsion direction, with the flexing direction providing relatively strong resistance to bending and the torsion direction providing relatively weak resistance to bending.

12. The biopsy needle assembly according to claim 10, wherein said biopsy needle is formed as one piece.

\* \* \* \* \*